CHRYSANTHEMUM PLANT
Filed April 24, 1972 5 Sheets-Sheet 1
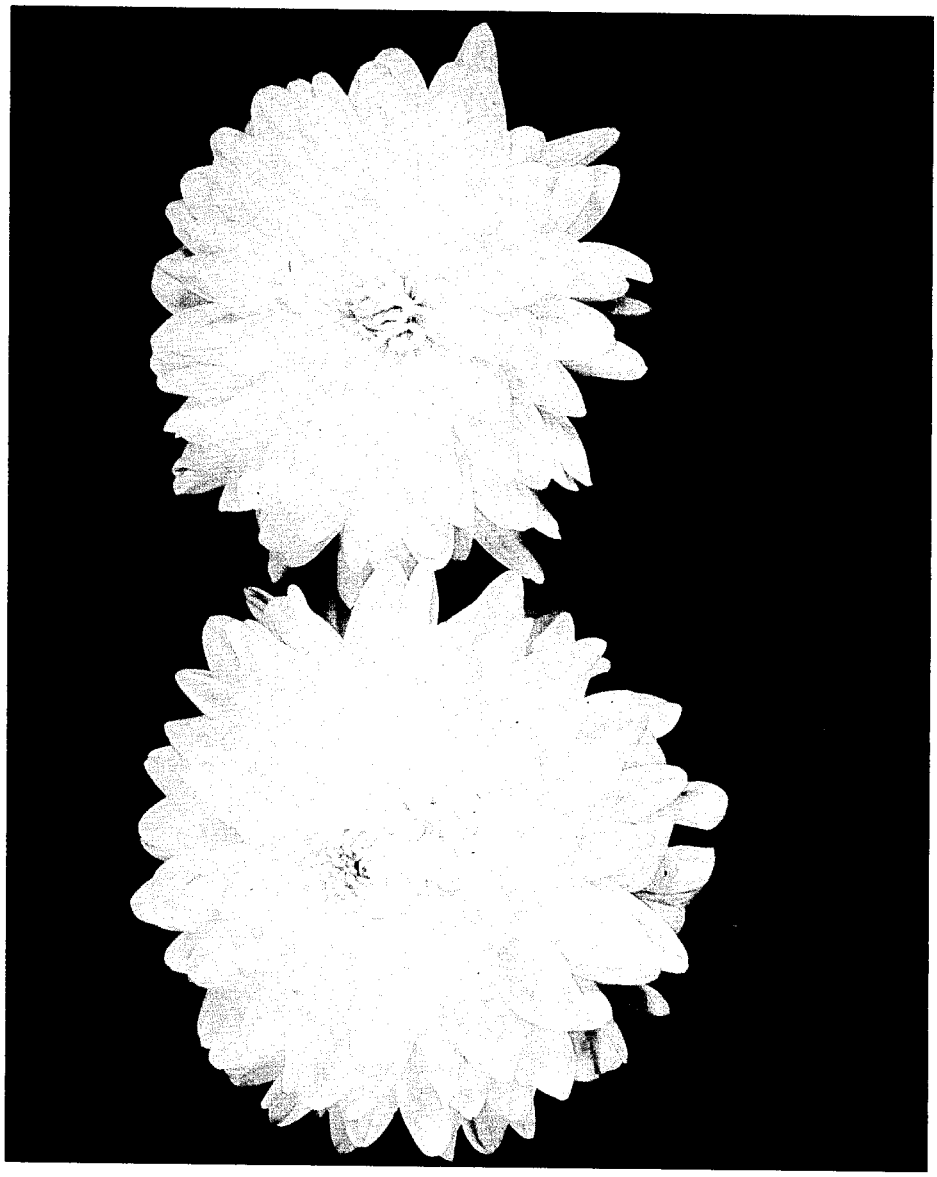

CHRYSANTHEMUM PLANT
Filed April 24, 1972
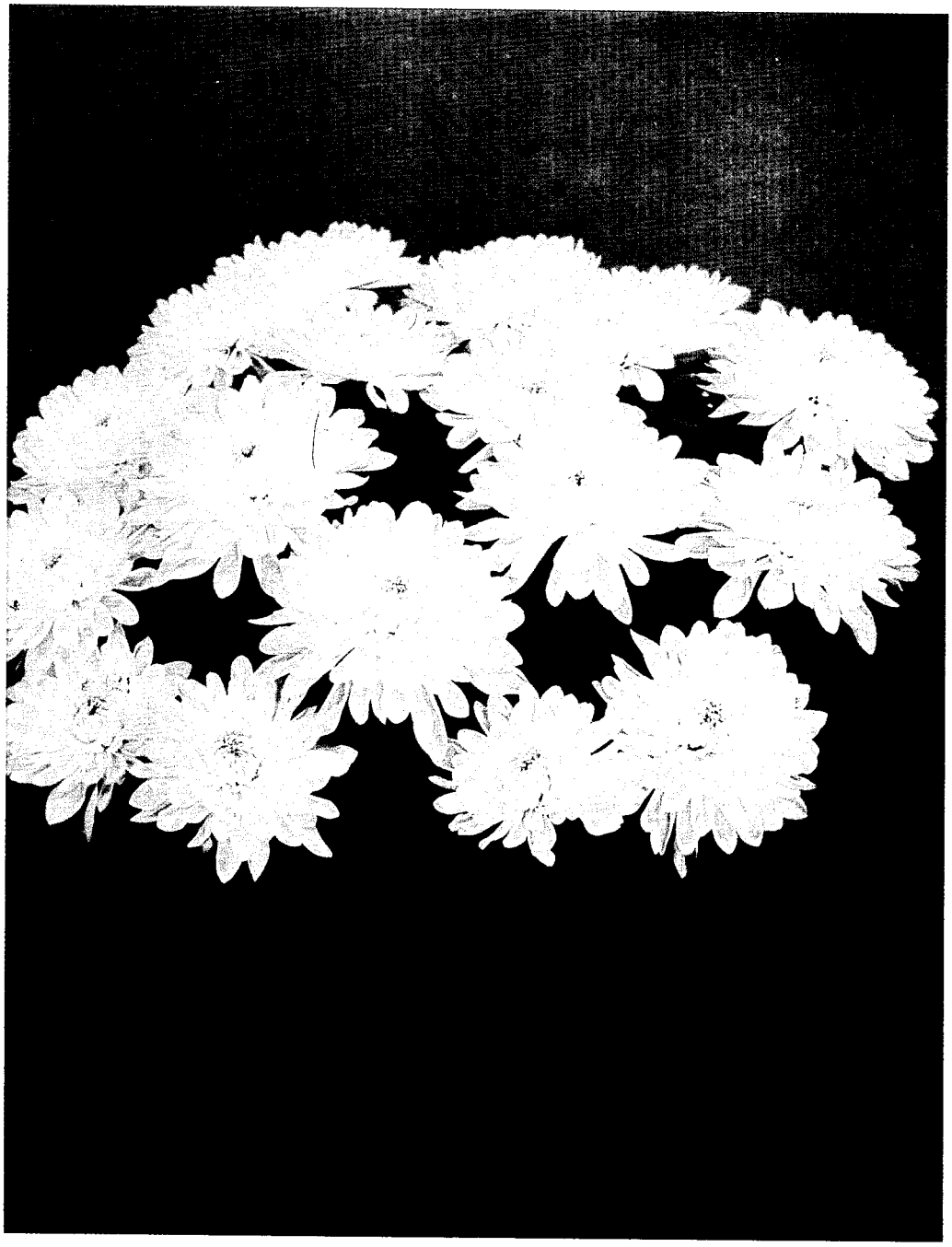

CHRYSANTHEMUM PLANT
Filed April 24, 1972 5 Sheets-Sheet 3
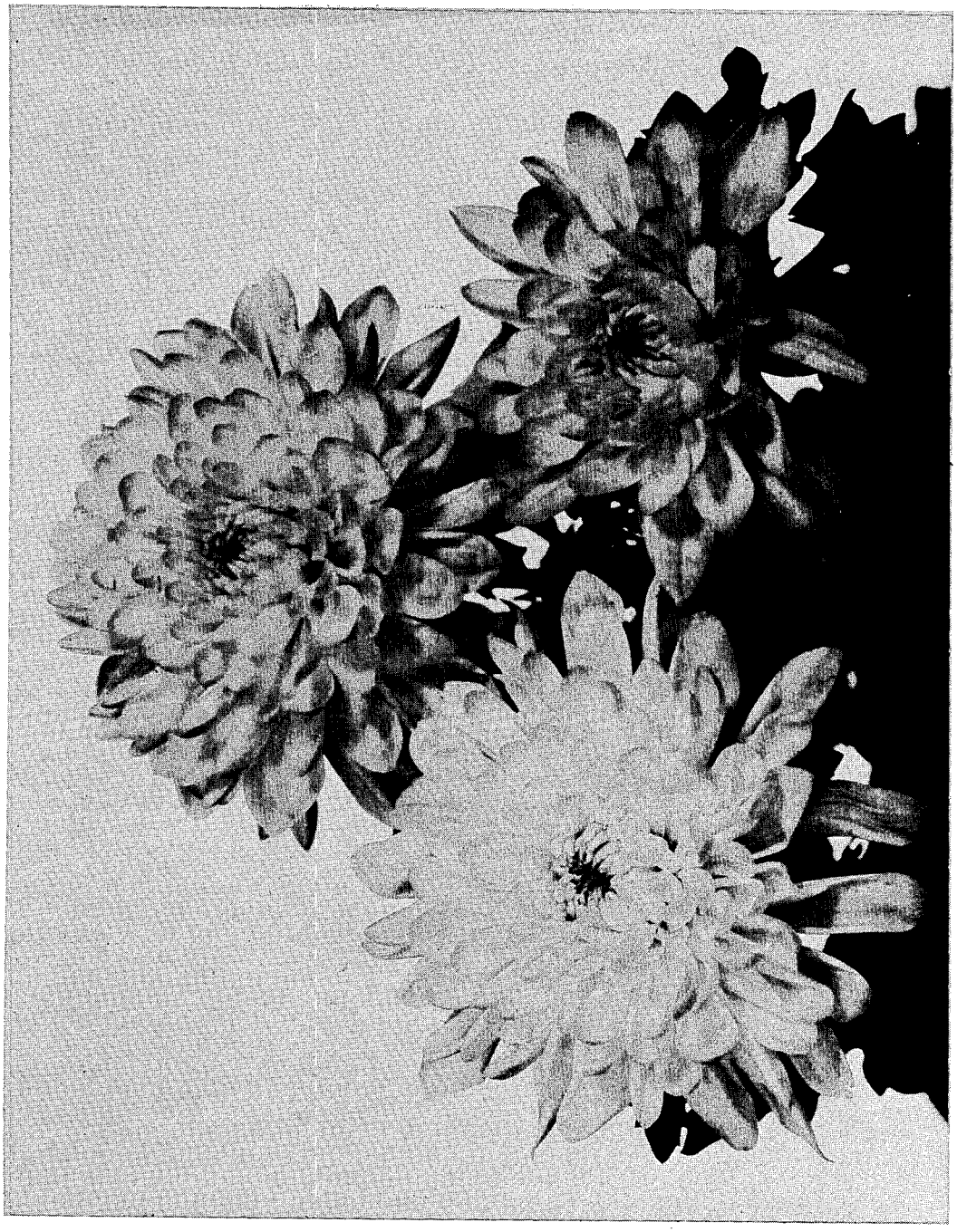

CHRYSANTHEMUM PLANT
Filed April 24, 1972 5 Sheets-Sheet 4
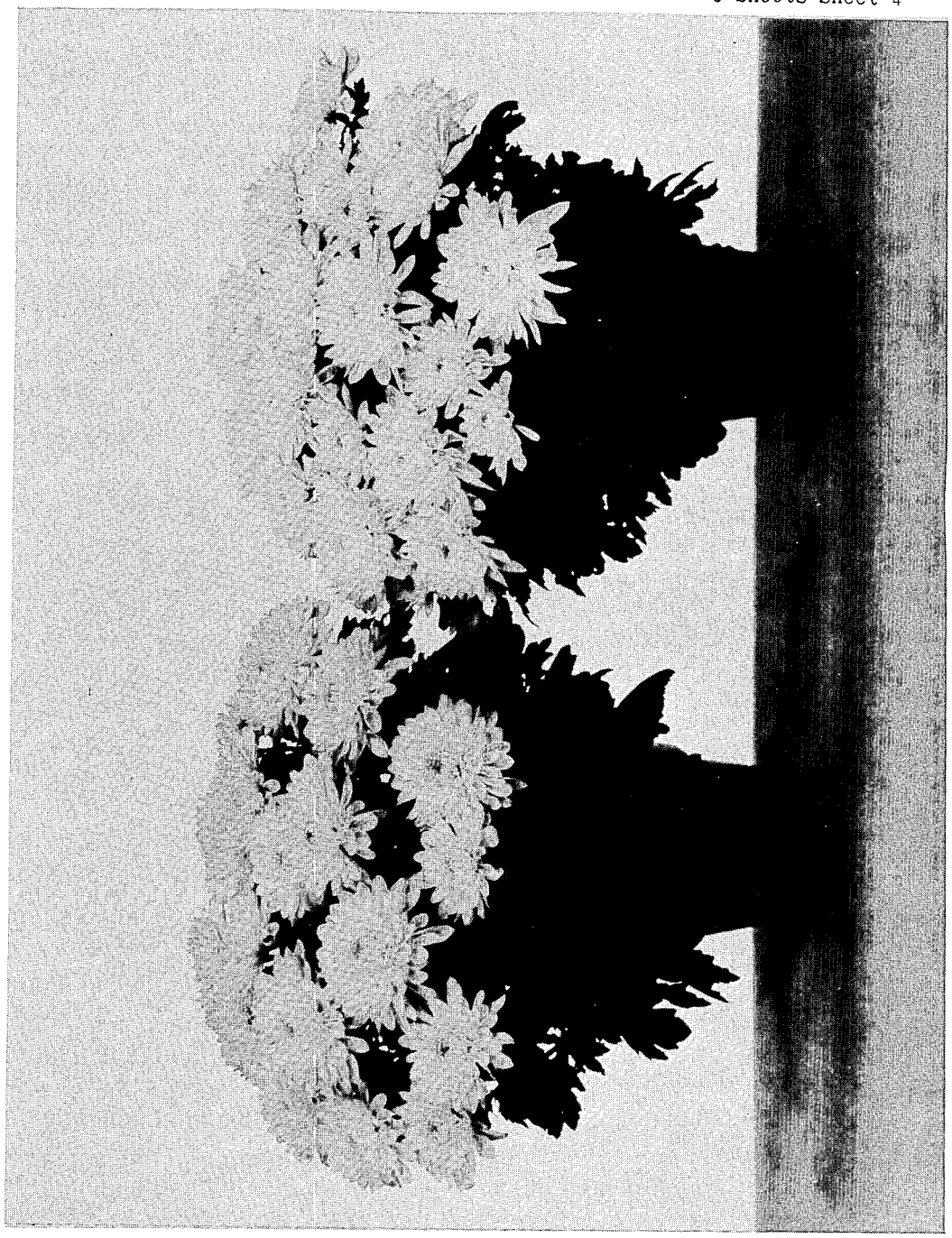

CHRYSANTHEMUM PLANT
Filed April 24, 1972
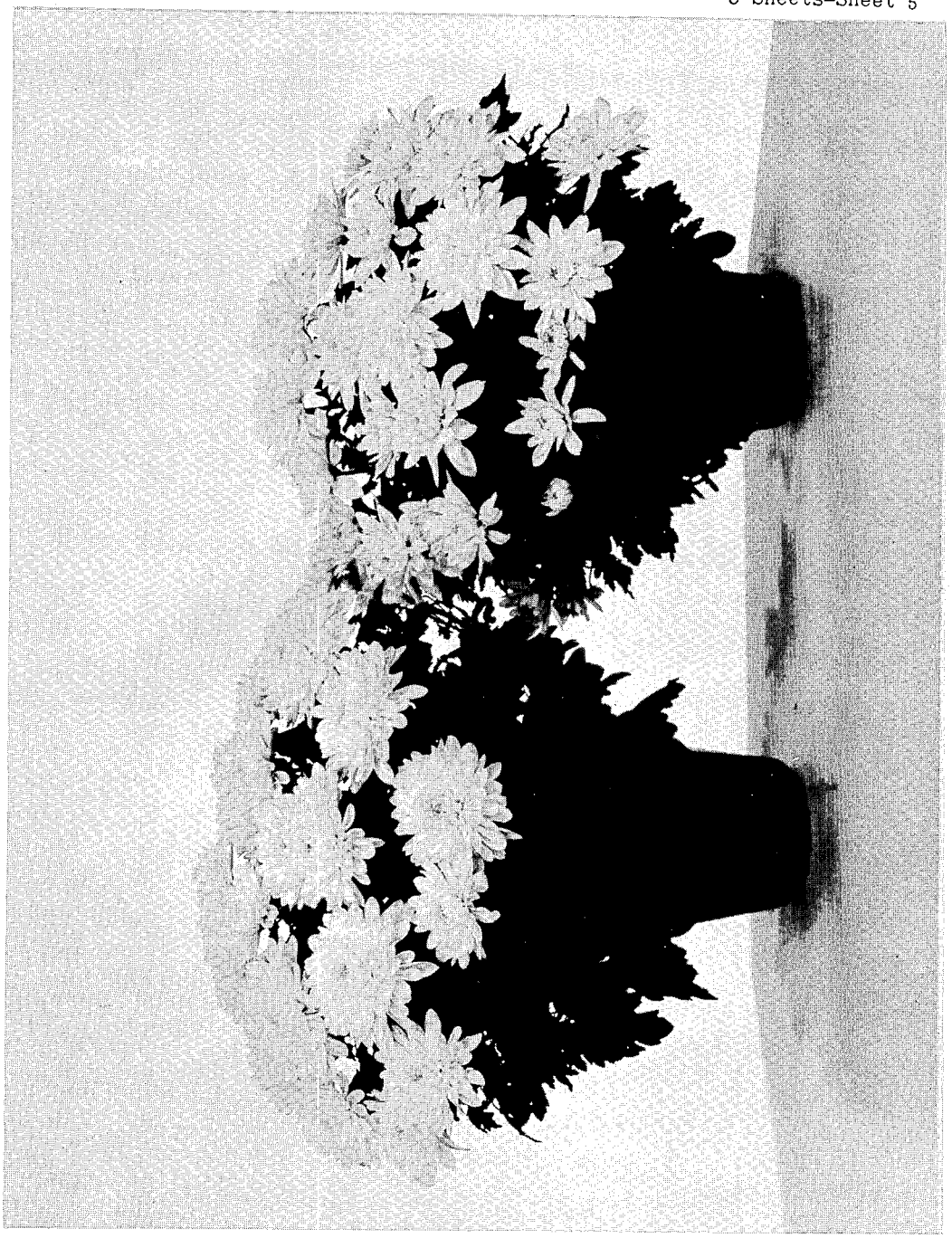

United States Patent Office

Plant Pat. 3,458

Patented Jan. 29, 1974

3,458

CHRYSANTHEMUM PLANT

Walter H. Jessel, Jr., Doylestown, and William E. Duffett, Akron, Ohio, assignors to Yoder Brothers, Inc., Barberton, Ohio

Filed Apr. 24, 1972, Ser. No. 247,193

Int. Cl. A01h *5/00*

U.S. Cl. Plt.—78 1 Claim

The present invention comprises a new and distinct cultivar of chrysanthemum plant which is a sport of the cultivar known in the United States as Mountain Snow, disclosed and claimed in our pending U.S. application Ser. No. 80,823, filed Oct. 12, 1970 (now P.P. 3,215).

The new cultivar is similar in many respects to the parent Mountain Snow, having the same characteristics of:

(1) Foliage size, shape and color.
(2) Asimilar growth habit.
(3) An identical recommended flowering period and a similar response.
(4) Approximately the same flower size and form.

The new cultivar is distinguished from Mountain Snow by its yellow flower color.

The new cultivar is also similar in certain respects to Mountain Sun, disclosed and claimed in our pending U.S. application Ser. No. 100,556, filed Dec. 21, 1970 (now P.P. 3,250), having the same characteristics of:

(1) Identical yellow flower color.
(2) Foliage shape and color.

The new cultivar is distinguished from Mountain Sun by the following characteristics, when grown under comparable conditions:

(1) Flowers approximately ¼″ larger at the two-thirds open stage to 1¼″ when fully mature and expanded with the flower form being more incurved than Mountain Sun.
(2) A petal up to approximately 5/16″ broader in width.
(3) Approximately 10–15% more petals, thereby providing a fuller flower.
(4) Leaves ¾″ longer in length.
(5) Approximately 2″–3″ taller habit.
(6) Approximately 1″ less spread as a pinched plant.
(7) A somewhat earlier response.

The new cultivar was selected from a flowering block of the parent cultivar at Barberton, Ohio; and when asexually reproduced by cuttings at Barberton, Ohio, has been found to retain its distinctive characteristics through successive propagations.

Our new cultivar when grown in the vicinity of Barberton, Ohio, has a response period of approximately 10 weeks, and the following detailed description is based on observations made of the new cultivar in a greenhouse in Barberton, Ohio. The response time, blooming, period, color, and total vigor may vary significantly with varying environmental conditions such as temperature, daylength, and light intensity. Suggested flowering in the northern and western United States is from January through December, with the best flowering period being from mid-March through November. Like Mountain Sun and Mountain Snow, it tends to develop a longitudinal petal roll December, January and February during low light periods. In the south, the suggested flowering period is January through December; and in Florida, December through April.

The accompanying drawings show the unique characteristics of our new cultivar, with the color in the color photographic drawings being as true as possible with color illustrations of this type. Sheet 1 comprises a comparison photograph, with the new cultivar appearing on the left and the cultivar Mountain Sun on the right. Sheet 2 comprises a color photograph of the new cultivar by itself. Sheet 3 comprises a black and white comparison photograph, with the parent cultivar Mountain Snow appearing in the lower left, the new cultivar appearing in the top center, and the comparison cultivar Mountain Sun appearing in the lower right. The similarity in size and response of the new and parent cultivars will be noted, as will the later response of the cultivar Mountain Sun. Sheet 4 comprises a black and white comparison photograph showing the new cultivar and the parent cultivar Mountain Snow in pot form. The new cultivar is on the left and the parent cultivar Mountain Snow is on the right. The similarity in height, flower size, vigor, and response will be noted. Sheet 5 comprises a black and white comparison photograph showing the new cultivar on the left and the cultivar Mountain Sun on the right. The comparison photograph clearly illustrates the earlier response, taller habit, and more fully petalled flower form of the new cultivar when compared with Mountain Sun.

In the following detailed description, color references are made to the Munsell Color Book, 1963 edition, and comparisons are made with the cultivar Mountain Snow and Mountain Sun. Where only a single value or description appears for the new cultivar, such value or description applies as well to the comparison cultivars.

Botanical classification: *Chrysanthemum morifolium*

| | Mountain Peak | Mountain Snow | Mountain Sun |
|---|---|---|---|
| Bloom: | | | |
| Size | 5″ | 5″ | 4¾″. |
| Fully expanded | 6½″ | 6½″ | 5¼″. |
| Borne | Terminal on disbudded branches | | |
| Stems | Strong | | |
| Permanence | 10-12 days | | |
| Form | Decorative, equal to Mountain Snow. More incurved than Mountain Sun. | Decorative, equal to Mountain Peak. More incurved than Mountain Sun. | Decorative, less incurved than Mountain Peak or Mountain Snow. |
| Color: | | | |
| Center of flower | Dark yellow, 7.5Y8.5/12 | Light green, 2.5GY9/6 to ivory white 7.5Y9/2. | Dark yellow, 7.5Y8.5/12. |
| Base of petals | Dark yellow, 7.5Y8.5/12 | Light green, 2.5GY9/6 | Do. |
| Inside of petals | Yellow, 7.5Y8.5/8 to light yellow, 7.5Y9/6 | White, N9.5/ | Yellow, 7.5Y8.5/8 to light yellow, 7.5Y9/6. |
| Reverse of petals | Light yellow, 7.5Y9/6 | do | Light yellow, 7.5Y9/6. |
| Tonality from a distance. | Yellow | White | Yellow. |
| Discoloration | Light yellow, 7.5Y9/6 | White, N9.5/ | Light yellow, 7.5Y9/6. |
| Petals: | | | |
| Texture | Smooth | | |
| Appearance and form | Open at base, broadening quickly to 1 1/16″ wide, very broad, shallow keel. | Open at base, broadening quickly to 1 1/16″ wide, very broad, shallow keel. | Open at base, broadening to ¾″ wide broad shallow keel. |
| Arrangement | Composite, whorled on a single receptacle | | |
| Persistence | Resist shatter | | |
| Fragrance | Typical chrysanthemum | | |

TABLE—Continued

| | Mountain Peak | Mountain Snow | Mountain Sun |
|---|---|---|---|
| Reproductive organs: | | | |
| Stamen, anthers | None to 30–40 | | |
| Pollen | None to very scant | | |
| Arrangement | Clustered in center of flower, if present | | |
| Styles | Present both ray and disc florets | | |
| Length | Short | | |
| Ovaries | At the base of petal attached to receptacle | | |
| Plant: | | | |
| Form | Herbaceous | | |
| Growth | Semi-upright | | |
| Height | Approximately 15½″ when given 10 week medium to tall treatment timing as defined in the timetables of Yoder Brothers, Inc., Barberton, Ohio, for the various seasons of the year. | Approximately 15½″ when given 10 week medium to tall treatment timing as defined in the timetables of Yoder Brothers, Inc., Barberton, Ohio, for various seasons of the year. | Approximately 13″ when given 10 week medium to tall treatment timing as defined in the timetables of Yoder Brothers, Inc., Barberton, Ohio, for the various seasons of the year. |
| Spread | Approximately 8½″ when given 10 week medium to tall treatment timing as defined in the timetables of Yoder Brothers, Inc., Barberton, Ohio, for the various seasons of the year. | Approximately 8½″ when given 10 week medium to tall treatment timing as defined in the timetables of Yoder Brothers, Inc., Barberton, Ohio, for the various seasons of the year. | Approximately 9½″ when given 10 week medium to tall treatment as defined in the timetables of Yoder Brothers, Inc., Barberton, Ohio, for the various seasons of the year. |
| Foliage: | | | |
| Top side | Green, 7.5GY3/4 | | |
| Size | 5″ long, 3″ wide | 5″ long, 3″ wide | 4¼″ long, 2¾″ wide. |
| Quantity | Numerous | | |
| Shape | Spatulate lobed | | |
| Texture | Smooth | | |
| Ribs and veins | Slight prominence | | |
| Edge | Slighty indented | | |
| Serration | Very slight | | |
| Under side | Light greem, 7.5GY5/4 | | |
| Stipules | Very prominent | | |

We claim:

1. A new and distinct cultivar of chrysanthemum characterized particularly as to uniqueness when compared to the parent cultivar Mountain Snow by its yellow flower color, and being unique relative to the cultivar Mountain Sun by its ¼″–1¼″ larger flowers, 10–15% more petals which are approximately 5/16″ broader in width, approximately ¾″ longer leaves, by its approximately 2″–3″ taller habit and 1″ less spread as a pinched plant, by its somewhat earlier response, and by its more incurved flower form.

No references cited.

ROBERT E. BAGWILL, Primary Examiner